US00PP37222P3

(12) United States Plant Patent
Flore

(10) Patent No.: US PP37,222 P3
(45) Date of Patent: Jan. 20, 2026

(54) ***PHALAENOPSIS* PLANT NAMED 'MI02909'**

(50) Latin Name: *Phalaenopsis hybrida*
Varietal Denomination: MI02909

(71) Applicant: MICROFLOR N.V., Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 19/096,418

(22) Filed: Mar. 31, 2025

(65) Prior Publication Data

US 2025/0311650 P1 Oct. 2, 2025

Related U.S. Application Data

(60) Provisional application No. 63/572,673, filed on Apr. 1, 2024.

(51) Int. Cl.
*A01H 5/02* (2018.01)
*A01H 6/62* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./311
See application file for complete search history.

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'MI02909', characterized by upright plant habit; leaves that are semi-erect in orientation; upright flowering stems; freely flowering habit with typically about two inflorescences per plant, each inflorescence with numerous flowers; and white-colored flowers with irregular and variable dark-reddish purple-colored spots.

2 Drawing Sheets

REFERENCED TO CLOSELY-RELATED APPLICATIONS

Figure 1:
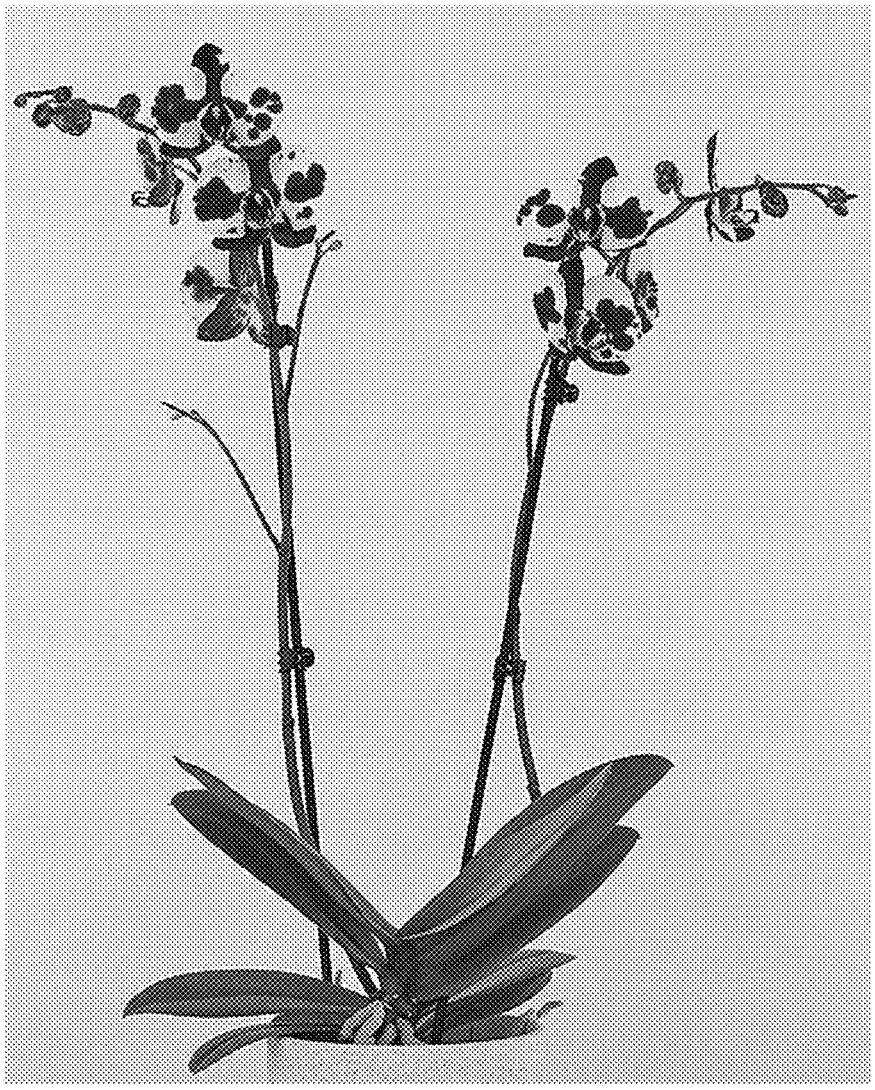

A Provisional U.S. Patent Application for the instant plant was filed by the Inventor and Applicant on Apr. 1, 2024, application Ser. No. 63/572,673. Domestic priority is claimed to this Provisional U.S. Patent Application.

Botanical designation: *Phalaenopsis hybrida.*

Cultivar denomination: 'MI02909'.

BACKGROUND OF THE INVENTION

The present invention relates to a new and distinct cultivar of *Phalaenopsis* plant, botanically known as *Phalaenopsis hybrida*, and hereinafter referred to by the name 'MI02909'.

The new *Phalaenopsis* plant is a product of a planned breeding program conducted by the Inventor in Lochristi, Belgium. The objective of the breeding program is to develop new fast-growing and freely flowering *Phalaenopsis* plants with flowers with unique patterns and coloration.

The new *Phalaenopsis* plant originated from a cross-pollination in December 2016 in Lochristi, Belgium of a proprietary selection of *Phalaenopsis hybrida* identified as code number PH02185, not patented, as the female, or seed, parent with a proprietary selection of *Phalaenopsis hybrida* identified as code number PH03087, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in December 2019.

Asexual reproduction of the new *Phalaenopsis* plant by in vitro meristem propagation in a controlled environment in Lochristi, Belgium since January 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI02909'. These characteristics in combination distinguish 'MI02909' as a new and distinct *Phalaenopsis* plant:

1. Upright plant habit.
2. Leaves that are semi-erect in orientation.
3. Upright flowering stems.
4. Freely flowering habit with typically about two inflorescences per plant, each inflorescence with numerous flowers.
5. White-colored flowers with irregular and variable dark-reddish purple-colored spots.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are shorter than leaves of plants of the female parent selection.
2. Plants of the new *Phalaenopsis* are more freely flowering than plants of the female parent selection.
3. Plants of the new *Phalaenopsis* have smaller flowers than plants of the female parent selection.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are shorter than leaves of plants of the male parent selection.
2. Plants of the new *Phalaenopsis* are more freely flowering than plants of the male parent selection.
3. Plants of the new *Phalaenopsis* have smaller flowers than plants of the male parent selection.

Plants of the new *Phalaenopsis* can be compared to plants of *Phalaenopsis hybrida* 'Elegant Polka Dots', not patented. In side-by-side comparisons, plants of the new *Phalaenopsis* differ primarily from plants of 'Elegant Polka Dots' in the following characteristics:

1. Leaves of plants of the new *Phalaenopsis* are semi-erect in orientation whereas leaves of plants of 'Elegant Polka Dots' are horizontal to drooping in orientation.
2. Petal apices of plants of the new *Phalaenopsis* are rounded whereas petal apices of plants of 'Elegant Polka Dots' are more obtuse.
3. Central lobes of the flower labellum of plants of the new *Phalaenopsis* are white and yellow in color with red purple-colored margins whereas central lobes of the flower labellum of plants of 'Elegant Polka Dots' are white and yellow in color with reddish orange-colored margins.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'MI02909' grown in a container.

Figure 2:
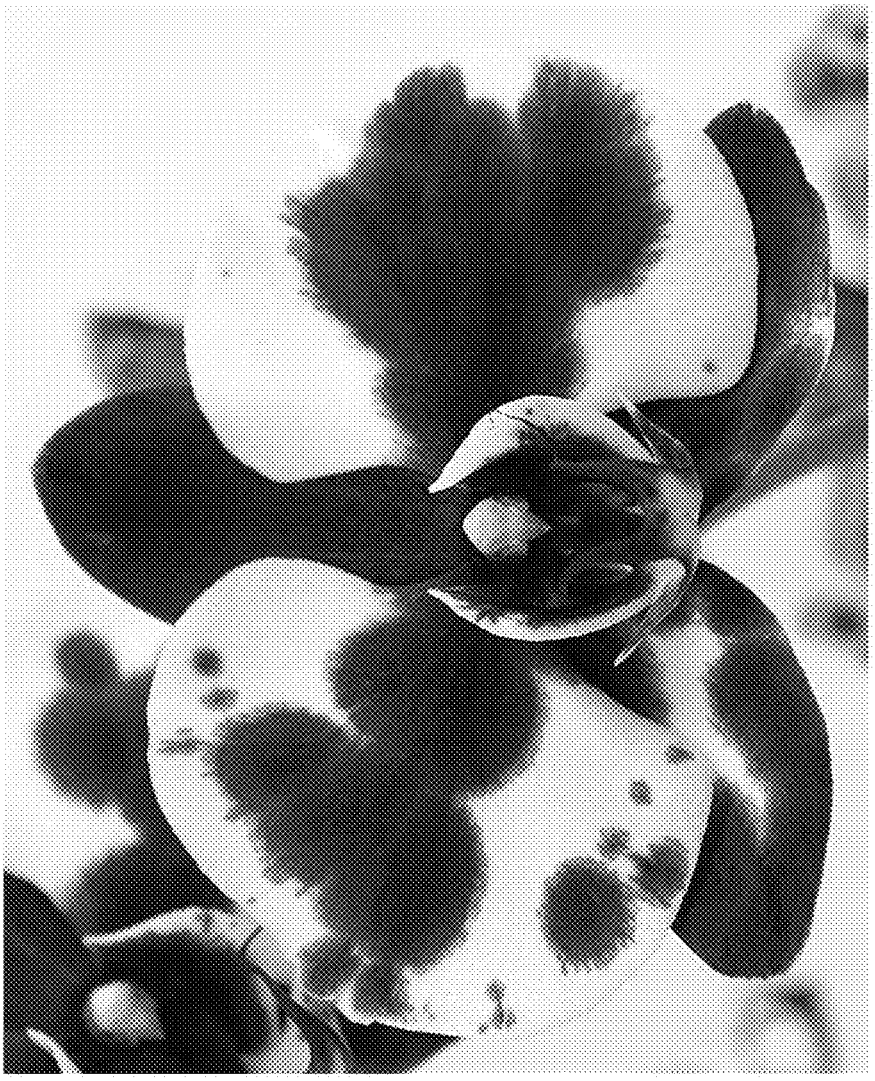

The photograph on the second sheet (FIG. 2) is a close-up view of typical flowers of 'MI02909'.

DETAILED BOTANICAL DESCRIPTION

The aforementioned photographs and following observations and measurements describe plants grown during the early autumn in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/$m^2$ to 375 Watt/$m^2$. Plants were 76 weeks old when the photographs and the detailed description were taken. In the following description, color references are made to The Royal Horticultural Society Colour Chart, 2001 Edition, except where general terms of ordinary dictionary significance are used.

Botanical classification: *Phalaenopsis hybrida* 'MI02909'.

Parentage:

*Female parent*.—Proprietary selection of *Phalaenopsis hybrida* identified as code number PH02185, not patented.

*Male parent*.—Proprietary selection of *Phalaenopsis hybrida* identified as code number PH03087, not patented.

Propagation:

*Type*.—By in vitro meristem propagation.

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160 days at temperatures about 26° C.

*Time to produce a rooted young plant, winter*.—About 150 to 180 days at temperatures about 26° C.

*Root description*.—Thick, fleshy; actual color of the roots is dependent on substrate composition, water quality, fertilizer, substrate temperature and age of roots.

*Rooting habit*.—Small amount of branching; sparse.

Plant description:

*Plant form and growth habit*.—Herbaceous epiphyte; upright plant habit with typically two inflorescences per plant, each inflorescence with numerous flowers; monopodial.

*Plant height, substrate level to top of foliar plane*.—About 18 cm.

*Plant height, substrate level to top of inflorescences*.—About 53.5 cm.

*Plant diameter or spread*.—About 36 cm.

Leaf description:

*Arrangement and quantity*.—Distichous, simple; sessile; about nine leaves per plant.

*Length*.—About 17.5 cm.

*Width*.—About 7.1 cm.

*Aspect*.—Semi-erect.

*Shape*.—Elliptic.

*Apex*.—Obtuse to unequal obtuse.

*Base*.—Sheathed.

*Margin*.—Entire.

*Texture and luster, upper and lower surfaces*.—Smooth, glabrous; glossy.

*Venation pattern*.—Camptodromous.

*Color*.—When opening, upper surface: Close to 137A. When opening, lower surface: Close to 138A; marginal edges, close to 177A. Fully expanded leaves, upper surface: Close to 137A; venation, close to 137A. Fully expanded leaves, lower surface: Close to 138A; venation, close to 138A.

Inflorescence description:

*Appearance and flowering habit*.—Showy zygomorphic flowers arranged on axillary branched racemes; typically two inflorescences per plant; each inflorescence with about eleven to twelve flowers; flowers face outwardly on arching inflorescences supported by upright peduncles; flowers with three petals, two lateral petals and one center petal transformed into a labellum and three sepals.

*Fragrance*.—To date, none detected.

*Time to flower*.—Plants begin flowering about 17 weeks after an eight-week inductive cooling period; flowers open about five weeks after flower buds develop.

*Flower longevity*.—Long flowering period and long shelf life as individual flowers last for about 13 weeks on the plant; flowers not persistent.

*Inflorescence length* (*lowermost flower to inflorescence apex*).—About 24 cm.

*Inflorescence width*.—Axially, about 36 cm and radially, about 30 cm.

*Flower buds*.—Height: About 2 cm. Diameter: About 1.8 cm. Shape: Ovate. Color: Close to 150C; spots, close to 187A.

*Flower diameter*.—About 8.6 cm.

*Flower depth*.—About 3.1 cm.

*Petals, quantity and arrangement*.—Three, two lateral petals and one center petal transformed into a labellum; petals free and not imbricate.

*Lateral petals*.—Length: About 3.7 cm. Width: About 4.9 cm. Shape: Roughly flabellate. Apex: Rounded. Margin: Entire. Texture and luster, upper and lower surfaces: Smooth, glabrous, velvety; matte. Color: When opening, upper and lower surfaces: Close to 155C; random and variable spots, close to 59A. Fully opened, upper and lower surfaces: Close to 155C; random and variable spots, close to 59A; color does not change with subsequent development.

*Labella*.—Appearance: Tri-lobed with two lateral lobes and a central lobe. Central lobe length: About 1.9 cm. Central lobe width: About 2.5 cm. Shape, lateral lobes: Oblanceolate; apices, obtuse; and margins, entire. Shape, central lobe: Trullate; apices, cleft with short and narrow recurved cirrhose tips; margins, entire. Texture and luster, upper and lower surfaces: Smooth, glabrous, moderately velvety; matte. Callosities: Located at the base of the labellum and attachment point of the lateral petals; about 5 mm in length, about 4 mm in width and about 4 mm in height. Color, central lobe: When opening and fully opened, upper surface: Center, close to 155C; towards the margins, close to 59A; towards the base, close to 4B. When opening and fully opened, lower surface: Center, close to 155C; towards the margins, close to 59A; towards the base, close to 4B. Color, lateral lobes: When opening and fully opened, upper surface: Close to 59A; toward the margins, 4B and 155C. When opening and fully opened, lower surface: Close to 59A; toward the margins, 4B and 155C. Color, callosities: Close to 59A.

*Sepals*.—Quantity and arrangement: Three, two lower lateral sepals and one upper dorsal sepal. Length, lateral sepal: About 3.9 cm. Width, lateral sepals: About 2.3 cm. Length, dorsal sepal: About 3.8 cm. Width, dorsal sepal: About 2.4 cm. Shape, lateral sepals: Ovate. Shape, dorsal sepal: Elliptical. Apex, lateral sepals: Bluntly acute. Apex, dorsal sepal: Obtuse. Base, lateral and dorsal sepals: Rounded. Margin, lateral and dorsal sepals: Entire. Texture and luster, lateral and dorsal sepals, upper and lower surfaces: Smooth, glabrous, velvety; matte. Color, lateral and dorsal sepals: When opening, upper surface: Close to 187A; random and variable patches, close to 155C. When opening, lower surface: Close to 59A; random and variable patches, close to 157B. Fully opened, upper and lower surfaces: Close to 187A; random and variable patches, close to 155C; color does not change with subsequent development.

*Peduncles*.—Length: About 52 cm. Diameter, proximally: About 6 mm. Aspect: Mostly upright. Texture and luster: Smooth, glabrous; matte. Color: Close to 200C.

*Pedicels*.—Length: About 4.1 cm. Diameter: About 3 mm. Aspect: About 90° from peduncle axis. Texture and luster: Smooth, glabrous; matte. Color: Proximally, close to 59A and distally, close to 156C.

*Reproductive organs*.—Androecium: Column length: About 8 mm. Column width: About 6 mm. Column color: Close to 59A; distally, close to 155C. Pollinia quantity: Two. Pollinia diameter (per two pollinia): About 2 mm. Pollinia color: Close to 24A. Gynoecium: Stigma length: About 3 mm. Stigma width: About 3 mm. Stigma shape: Reniform. Stigma color: Close to 76D. Ovary length: About 1.5 cm. Ovary diameter: About 3 mm. Ovary color: Initially, close to 156A; becoming closer to 156C with subsequent development. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and to be suitable for USDA Hardiness Zones 10 and higher.

It is claimed:

1. A new and distinct *Phalaenopsis* plant named 'MI02909' as herein illustrated and described.

* * * * *